US008486026B2

(12) United States Patent
Koberstein

(10) Patent No.: US 8,486,026 B2
(45) Date of Patent: Jul. 16, 2013

(54) INTRAVENOUS CATHETER ANCHOR SYSTEM AND METHOD

(76) Inventor: John Koan Koberstein, Albany, OR (US)

( * ) Notice: Subject to any disclaimer, the term of this patent is extended or adjusted under 35 U.S.C. 154(b) by 435 days.

(21) Appl. No.: 12/954,158

(22) Filed: Nov. 24, 2010

(65) Prior Publication Data

US 2011/0125098 A1    May 26, 2011

Related U.S. Application Data

(60) Provisional application No. 61/264,611, filed on Nov. 25, 2009.

(51) Int. Cl.
*A61M 5/32* (2006.01)
(52) U.S. Cl.
USPC ............. 604/179; 604/174; 604/177; 604/34; 604/180; 604/250; 128/876; 128/877
(58) Field of Classification Search
USPC ................. 604/174–180, 34, 250; 128/876, 128/877
See application file for complete search history.

(56) References Cited

U.S. PATENT DOCUMENTS

2004/0082916 A1 *  4/2004  Jenkins ................. 604/174

* cited by examiner

*Primary Examiner* — Kevin C Sirmons
*Assistant Examiner* — Edelmira Bosques
(74) *Attorney, Agent, or Firm* — Dean A. Craine

(57) ABSTRACT

An improved anchor system and method for holding an intravenous catheter to the patient's body that is easier to clean. The system includes an intravenous catheter having a main line, a yoke attached to the main line, an elastic band made of non-porous material, and a neck lanyard with a clamp. During use, the elastic band is positioned around the two lumens and twisted into a figure eight configuration, forming two loops. Each lumen is extended into one of the elastic band's two loops. The lanyard's clamp is then attached to the crossover section of the elastic band located between the two loops. The elastic band is sufficient in size and resiliency so that when the clamp is released, each loop may be stretched so the lumens may be removed so the elastic band may be replaced.

4 Claims, 3 Drawing Sheets

US 8,486,026 B2

INTRAVENOUS CATHETER ANCHOR SYSTEM AND METHOD

This is a utility patent application that claims benefit of U.S. Provisional Application No. 61/264,611, filed on Nov. 25, 2009.

Notice is hereby given that the following patent document contains original material which is subject to copyright protection. The copyright owner has no objection to the facsimile or digital download reproduction of all or part of the patent document, but otherwise reserves all copyrights whatsoever.

BACKGROUND OF THE INVENTION

1. Field of the Invention

This invention pertains to devices used to hold the external components on an indwelling, intravenous catheter against a patient's body.

2. Description of the Related Art

An indwelling, intravenous catheter is used to administer chemotherapy, transfusions and intravenous feedings to a patient. A common intravenous catheter is a HICKMAN catheter sold by C.R. Bard Inc. of Murray Hill, New Jersey. Such catheters include a main line with a Y-shaped yoke attached to the exposed end of the main line that connects to two smaller lines, called 'lumens'. One end of the main line is inserted into the incisions formed on the chest wall and the jugular vein of the patient. A 'tunnel' is formed between the two incisions through which the main line is inserted. The main line is securely attached to a 'cuff' is implanted under the skin of the chest with the yoke and the two lumens extending outward and hung over the chest. Once implanted, it is important that the main line not be accidentally pulled out of the chest.

Each lumen includes an injection port at one end and a fluid shut off valve. The ends and the shut off valves cause the two lumens to naturally fall and extend downward over the chest if not supported. To support the two lumens and prevent the main line from being accidently pulled from the chest, the yoke and two lumens are wrapped or folded into a small bag that can be adhesively attached to the chest. The injection ends, the turn-off valves, the yoke and lumens are bulky objects when placed into a bag and uncomfortable when laid upon and are visible under clothing.

The ends of the lumens are injection sites and must be sterile. Sometimes, nurses have addressed both the chest support and the sterility issues by using tape and gauzes to cover the ends of the lumens and adhesively hold the yoke and the two lumens on the chest. One drawback with using tape and gauzes is they must be physically removed and adhesive residue may be left that must be thoroughly removed without pulling the main line from the incisions. Also, for patients with chest hair, removal of the tape and the adhesive residue from the skin can be uncomfortable.

What is needed is an improved anchor system for an indwelling intravenous catheter that loosely holds the yoke and two lumens over the chest in a partially draped configuration does not require using bags, pouches or adhesive tape.

SUMMARY OF THE INVENTION

An improved anchoring system and method for holding an indwelling intravenous catheter to the patient's body that loosely holds the yoke and two lumens in a partially draped configuration on the chest and without tape.

The system includes an elastic band made of non porous material and a neck lanyard with a clamp on one end. During use, the elastic band is twisted into a figure eight configuration and positioned around the two branch lines so each lumen extends and slides freely through one of the two loops. The elastic band is sufficient in size and resiliency so it may be easily stretched and removed for easy cleaning and repositioned. The size of the neck lanyard and the position of the clamp on the neck lanyard enable the clamp to be positioned over the chest so the two lumens bend upward from the incision site and over the sternum. The clamp includes two jaws that extend around the crossover section between the two loops formed when the elastic band is twisted into a figure eight configuration. When the clamp's two jaws are compressed against the crossover section, the elasticity of the band and the size of each loop is reduced so each loop tighten around a lumen. When the jaws of the clamp are opened and released from the elastic band, the loops expand enabling the two lumens to slide through so the elastic band may be replaced with a clean elastic band.

DESCRIPTION OF THE PREFERRED EMBODIMENT(S)

Figure 1:
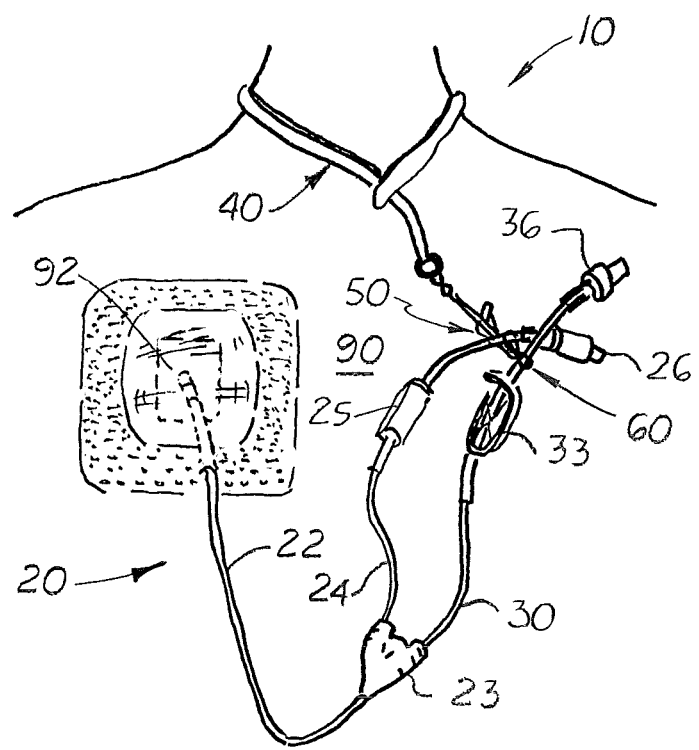
FIG. 1 is a front elevational view of a patient using the intravenous catheter anchor system disclosed herein.

Referring to the accompanying FIGS. 1-8, there is shown an improved catheter anchoring system 10 used to hold the yoke and two lumens used on an intravenous catheter 20 upward and against the patient's chest 90. The system 10 includes an intravenous catheter 20 that includes a main line 22 surgically implanted into the patient's chest 90. The end of main line 22 extends through an exit port 92 formed on the chest 90. Attached to the exposed end of the main line 22 is a three port yoke 23. Attached to two ports on the yoke 23 are two lumens 24, 30.

The system 10 also includes a neck lanyard 40 with a finger manipulated clamp 50 attached at one end. The neck lanyard 40 is rotated around the neck so the clamp 50 hangs downward over the chest 92 at a location at or slightly above the exit port 92. In one embodiment, the neck lanyard 40 is adjustable in length so the position of the clamp 50 over the chest 92 may be selectively adjusted.

The system 10 also includes an elastic band 60 made of non-porous material twisted into a figure eight configuration to form two equal size, interconnected loops 62, 64. During assembly, each lumen 24, 30 on the catheter 20 extends and slides freely through one of the two loops 62, 64, respectively.

The two jaws on the clamp 50 are then separated and the clamp 50 is perpendicularly aligned with the elastic band 60 so the cross over section of the elastic band 60 is positioned between the two jaws. When the jaws of clamp 50 are released the cross over section is forced together which further tightens the two loops 62, 64, around the two lumens 24, 30, respectively, securely holding the two loops 62, 64 around the two lumens 24, 30 and holding the two lumens 24, 30 in place over the chest 90 adjacent to the clamp 50. The elastic band 60 is sufficiently resilient so it may be selectively stretched to a sufficient size without breaking so two lumens 24, 30 maybe easily removed from the elastic band 60 so the elastic band 60 may be replaced and the lumens 24, 30 may be cleaned.

The elastic band 60 is similar to a small child hair band made of non-porous, chemical and heat resistant, synthetic material, such as polyurethane or urethane, capable of stretching four to five times its relaxed size. When relaxed, the elastic band 60 measures between 1.0 and 1.5 cm in length. The thickness of the elastic band 60 is approximately 2 to 5 mm. When the elastic band 60 is twisted into a figure eight configuration, two loops 62, 64 are formed. Before the clamp 50 is attached to the band 60, the two loops 24, 30 formed after twisting the elastic band 60 each measure approximately 1.5 cm in diameter.

Figure 2:
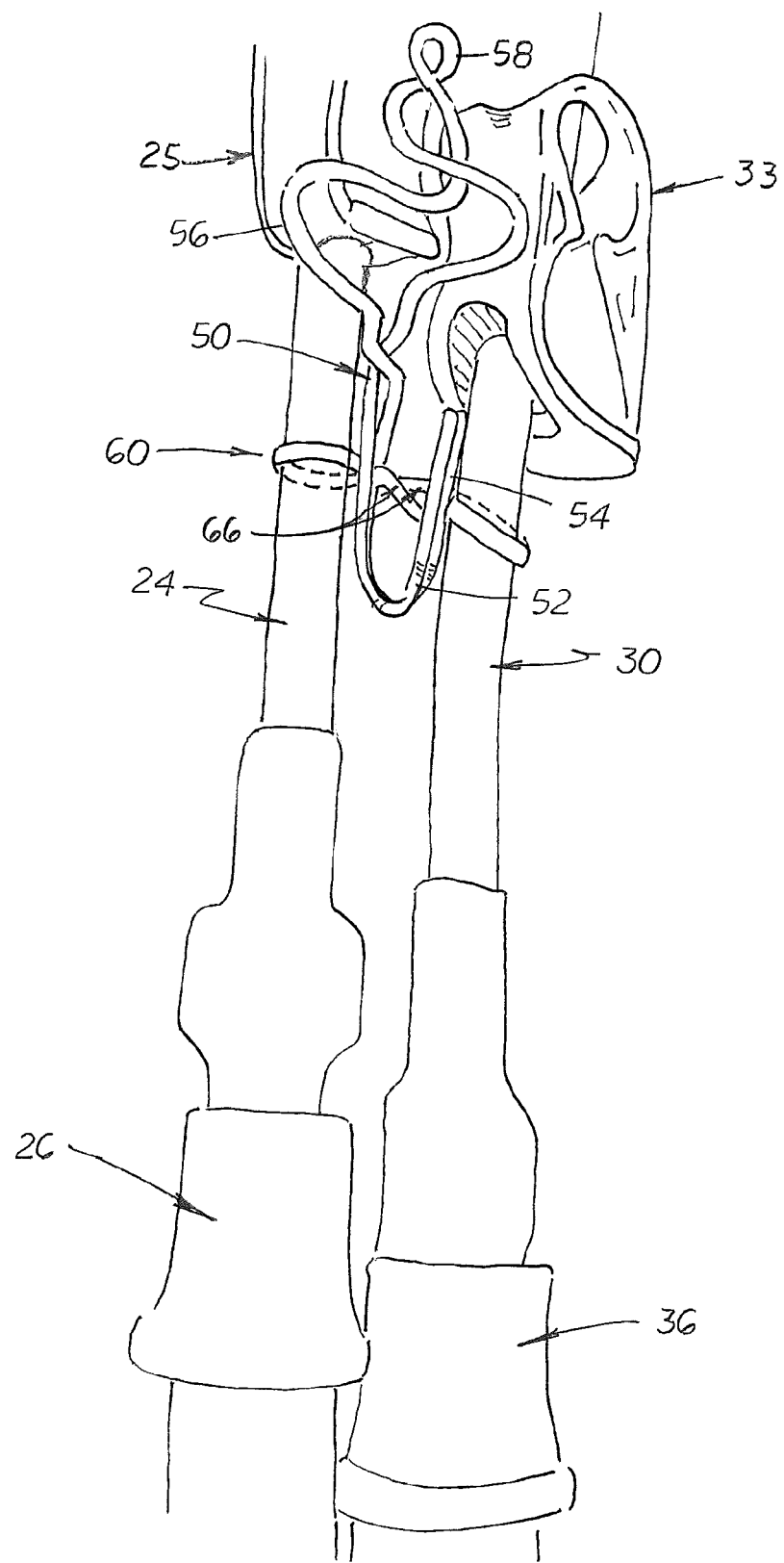
FIG. 2 is a top plan view of the clamp being attached to an elastic band attached to two lumens.
Figure 3:
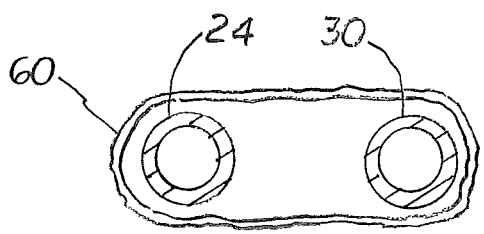
FIG. 3 is a sectional top plan view of the two branch lines showing a non-twisted elastic band placed around them.
Figure 4:
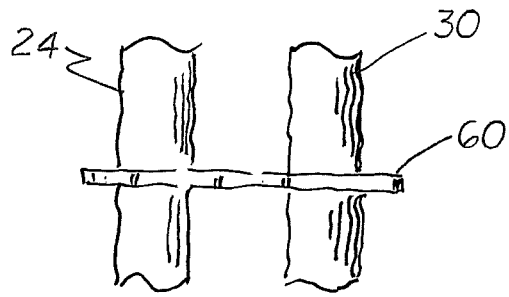
FIG. 4 is a side elevational view of the two branch lines and the elastic band shown in FIG. 3.
Figure 5:
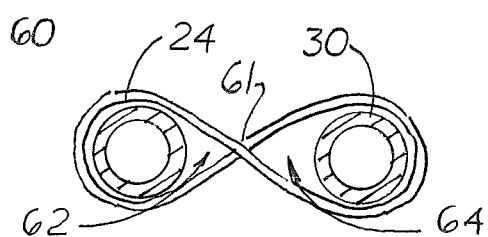
FIG. 5 is a sectional top plan view of the two lumens showing the elastic band twisted into a figure eight configuration with each lumen extended through a separate loop.
Figure 6:
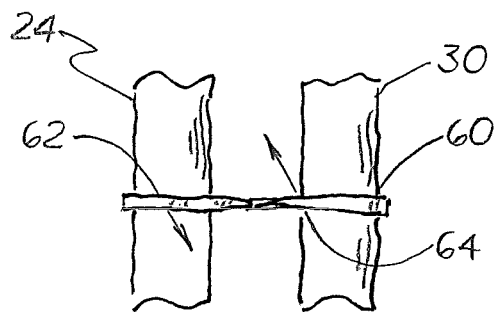
FIG. 6 is a side elevational view of the two lumens and the elastic band shown in FIG. 5.
Figure 7:
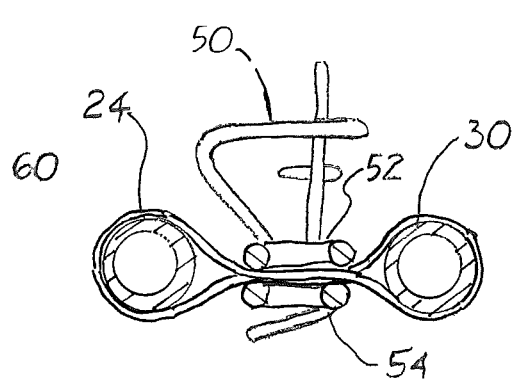
FIG. 7 is a sectional top plan view of the two lumens showing the elastic band twisted into a figure eight configuration with each branch line extended through a separate loop and showing a clamp with two jaws that compress the section of elastic band located between the two loops.
Figure 8:
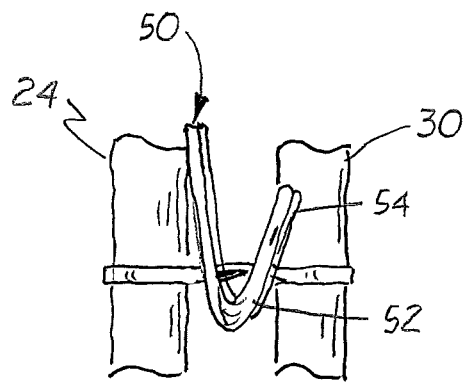
FIG. 8 is a side elevational view of the two lumens, the elastic band and the clamp shown in FIG. 7.

The manual clamp 50 is 'bull dog' style clamp with two flat or wide overlapping jaws 52, 54 that are resiliently pressed together. Integrally formed on each jaw 52, 54 is a handle 56, 58, respectively, which when forced together, open the two jaws 52, 54. The jaws 52, 54 are the same shape and are elongated narrow structures approximately 1 cm wide and 2 to 3 cm in length. During assembly, the clamp 50 is aligned between the two branch lines 24, 30, so that the two jaws 52, 54 are positioned between the two lumens 24, 30 and press on opposite sides of the crossing intermediate section 61 of the band 60 as shown in FIG. 2.

Because the two lumens 24, 30 are loosely supported over the chest 90, their locations over the chest 90 may be easily adjusted for comfort and different types of clothing.

Also disclosed herein is a method for supporting the two lumens 24, 30 on an indwelling intravenous catheter comprising the following steps:
 a. implanting a subcutaneous, intravenous catheter into the chest 90 of a patient, said intravenous catheter includes two lumens 24,30;
 b selecting a non-porous elastic band 60;
 c. twisting said band into a figure eight configuration to form two equal size loops 62, 64
 d. extending one said branch line through one said loop;
 e. selecting a neck lanyard with a clamp 50 attached at one end; and,
 f attaching said clamp 50 to the crossing intermediate section of said elastic band 60 thereby attaching said branch lines to said lanyard 40.

In compliance with the statute, the invention described herein has been described in language more or less specific as to structural features. It should be understood however, that the invention is not limited to the specific features shown, since the means and construction shown, is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. An improved intravenous catheter anchoring system for supporting the external yoke and lumens on the chest wall of a patient, comprising:
 a. an intravenous catheter that includes a main line that extends from an exit site on the chest wall of a patient, a yoke with at least one main line port and at two branch line ports, and two branch lines attached to said branch line ports;
 b. a non-porous elastic band twisted into a figure eight configuration to form two equal size loops with a crossover section located therebetween, each said loop being placed around one said branch line to hold said lumens in a side by side, parallel location;
 c. a neck lanyard extending around the neck of the patient and over a portion of the chest of the patient; and,
 d. a clamp attached to said neck lanyard and positioned over the chest over the patient, said clamp includes a pair of jaws that extend over the crossover section formed on said elastic band and between said loops reducing the diameter of said loops to securely attach said loops to said branch lines.

2. The improved intravenous catheter anchoring system, as recited in claim 1, wherein said elastic band measures between 1.0 and 1.5 cm in length and when twisted into a figure eight configuration forms two loops each measuring approximately 1.5 cm in diameter.

3. A support system for holding the lumens used on an indwelling intravenous catheter, comprising:
 a. a neck lanyard extending around the neck of the patient;
 b. a non-porous elastic band twisted into a figure eight configuration to form two equal size loops with a crossover section located therebetween, each said loop being placed around one lumen; and,
 c. a clamp attached to said neck lanyard and located over the chest of a patient with an indwelling catheter, said clamp includes a pair of flat jaws that extend over said crossover section formed on said elastic band and between said loops reducing the diameter of said loops to securely attach said loops to said lumens lines.

4. A method for anchoring the lumens used on an intravenous catheter to the chest of a patient, comprising the following steps:
 a. implanting a subcutaneous, intravenous catheter into the chest of a patient, said intravenous catheter includes two lumens;
 b selecting a non-porous elastic band;
 c. twisting said band into a figure eight configuration to form two equal size loops;
 d. extending one said branch line through one said loop;
 e. selecting a neck lanyard with a clamp attached at one end; and,
 f attaching said clamp to the crossing intermediate section of said elastic band attaching said branch lines to said lanyard.

* * * * *